United States Patent [19]

Jederström

[11] 3,997,467
[45] Dec. 14, 1976

[54] FOAM FORMING COMPOSITION

[75] Inventor: Gustaf Lennart Jederström, Bjorklinge, Sweden

[73] Assignee: Pharmacia Aktiebolag, Uppsala, Sweden

[22] Filed: May 21, 1974

[21] Appl. No.: 471,947

Related U.S. Application Data

[63] Continuation of Ser. No. 307,904, Nov. 20, 1972, abandoned.

[30] Foreign Application Priority Data

Nov. 26, 1971 Sweden ............................ 15217/71

[52] U.S. Cl. ........................ 252/305; 210/DIG. 26; 252/3; 252/8.05; 252/90; 252/307; 424/45
[51] Int. Cl.$^2$ ........................................ C09K 3/30
[58] Field of Search .............. 252/90, 305, 3, 8.05; 424/45

[56] References Cited

UNITED STATES PATENTS

| | | | |
|---|---|---|---|
| 2,655,480 | 10/1953 | Spitzer et al. | 252/90 |
| 2,995,521 | 8/1961 | Estignard-Bluard | 252/90 |
| 3,131,152 | 4/1964 | Klausner | 252/90 X |
| 3,553,138 | 1/1971 | Mace | 252/90 |

*Primary Examiner*—Richard D. Lovering
*Attorney, Agent, or Firm*—Fred Philpitt

[57] ABSTRACT

A foam forming composition consisting of a mixture of a hydrocarbon and/or a lipophilic hydrocarbon derivative, water, a liquified propellant and a surface active agent or mixture of such agents in such proportions as to obtain a mesomorphic phase, the surface active agent or agents being soluble in the water and the hydrocarbon and/or the lipophilic hydrocarbon derivative.

11 Claims, No Drawings

FOAM FORMING COMPOSITION

This is a continuation of application Ser. No. 307,904, filed Nov. 20, 1972, now abandoned.

The present invention is concerned with a composition for forming foam. The composition is especially adapted to be used for pressurized packaging for forming foams by spraying (aerosols). More particularly, the invention relates to a composition as indicated, consisting of a mixture comprising a hydrocarbon or a lipophilic hydrocarbon derivative or a mixture of such compounds, water, a liquefied propellant and a surface active agent or a mixture of such agents in such proportions as to obtain a mesomorphic phase.

The invention is characterized in that the surface active agent or mixture of such agents is soluble in water and in the hydrocarbon or the lipophilic hydrocarbon derivative or mixture thereof, said mesomorphic phase representing at least about 5 percent by weight of the mixture, and in that the propellant is dissolved in the mesomorphic phase in an amount of at least 2 percent by weight of the mixture.

The inventive composition enables extremely stable foam to be produced.

By the term "lipophilic hydrocarbon derivatives" is meant hydrocarbons containing one or more substituents which do not appreciably change the lipophilic properties of the hydrocarbon. Examples of such hydrocarbons and lipophilic hydrocarbon derivatives are p-xylene, 1-decanol, oleic acid, cholesterol, butanol and caprylic acid.

Three-component-systems comprising surface active agents, hydrocarbon and water forming mesomorphic phases are previously known (see Elworthy, PF; Florence A.T.; MacFarlane C.B., Solubilization by Surface Active Agents and its application in Chemistry and the Biological Sciences, page 110, published 1968 in Great Britain by Richard Clay Ltd. Rungay, Suffolk).

When preparing the composition of the present invention there is used a three-component-system for which the condition that the ingredients thereof shall form a mesomorphic phase is that their content in every particular case is selected between given limits dependent on the ingredients, as exemplified hereinafter; the percentages recited here and in the following relating to the total weight of the mixture of ingredients. For the system water, caprylic acid and 1-aminooctane, for example, a mesomorphic phase is obtained if the ingredients are present in the system within the following limits (1).

1. 10–60 % water
   1–55 % caprylic acid
   30–75 % 1-aminooctane.

When the three-component-system containing the mesomorphic phase is added with a varying quantity of the liquefied propellant dichlorotetrafluoroethane it is surprisingly found that it dissolved in the lamella structure of the mesomorphic phase and that upon expansion of the propellant the composition forms an extremely stable foam. Conditions in this respect are that the system contains a surface active agent capable of dissolving in water and hydrocarbons, at least approximately 5 % of mesomorphic phase, and that the liquefied propellant is dissolved in said phase in a quantity of at least 2 % of the total weight of the whole mixture.

In this instance, the ingredients should be selected between the following limits, in order to obtain the stable foam 2. 10–45 % water
   5–50 % caprylic acid
   40–85 % 1-aminooctane
   2–15 % dichlorotetrafluoroethane The same result will also be obtained with other liquefied propellants.

For other systems containing a surface active agent capable of dissolving in water and a hydrocarbon or a lipophilic hydrocarbon derivative, water and a hydrocarbon or a lipophilic hydrocarbon derivative it has been established that they form a mesomorphic phase within definite limits, depending on the type of ingredients, in which phase a liquefied propellant can be dissolved so as to produce a mixture, at least approximately 5 % of which represents the mesomorphic phase and in which the liquefied propellant is dissolved to at least approximately 2 % of the total weight of the mixture. The surprisingly high stability of the foam was found to be due to the fact that the mesomorphic phases have a lamella structure, which is also found in the foam.

Examples of other systems containing mesomorphic phases having a lamella structure in which liquefied propellants can be dissolved in accordance with the aforegoing are as follows:

3. 30–60 % water
   1–10 % p-xylene
   40–70 % 1-aminooctane
4. 20–80 % water
   1–25 % 1-decanol
   20–80 % sodium oleate
5. 15–40 % water
   15–30 % oleic acid
   20–70 % decaethylene glycol
6. 30–50 % water
   10–30 % butanol
   30–50 % sodium caprylate
7. 1–50 % water
   1–22 % cholesterol
   40–95 % lecithin Liquefied propellants are added to these three-component-systems (3), (4), (5), (6) and (7) in a manner similar to what applies to system (2) to form mixtures comprising mesomorphic phases having the propellant dissolved therein, said mixtures being capable of forming extremely stable foams.

Examples of liquefied propellants which can be used as ingredients when preparing the composition of the present invention, include fluoro and/or chloro-substituted lower saturated aliphatic hydrocarbons, in particular alkanes containing at most 4 carbon atoms and at least one fluorine atom and mixtures thereof and light hydrocarbons. Particular mention can be made in this respect, for example, to dichlorodifluoromethane, dichlorotetrafluoroethane and octafluorocyclobutane. Propane, isobutane, pentane, isopentanes, n-hexane are examples of unsubstituted hydrocarbons which can be used to advantage when preparing, for example, the compositions, (3), (5) and (7) above.

The surface active substances used in the aforegiven examples of systems are 1-aminooctane, sodium oleate, decaethylene glycol, sodium caprylate and lecithin.

The composition of the present invention can be used for many purposes where foam is required. The foam produced by the inventive composition is extremely stable and has a long-term durability. It can be used, for example, for the production of chemical-technical preparations and within the medical field, e.g. for pharmaceutical preparations. In certain instances other additives can be incorporated into the inventive composition, such as inert substances or therapeutically active substances or substances active in some other manner, such as catalysts. The compositions of the present invention can thus be used when producing foam plastics, the stable foam facilitating hardening of the plastics. The inventive compositions can also be used to produce foam for removing oil discharged on water. In this latter instance the purpose of the foam is to render the oil harmless by lifting it from the water, so that the oil can be burned avoiding the cooling effect of the water. Compositions according to the invention can also be used to produce combustible foam. Other compositions can be used for fire fighting. Another field of use is for producing therapeutical preparations, the foam formation being utilized, for example, for obtaining a wide contact surface. The invention also enables the preparation of compositions having excellent penetrating capability.

The composition of the present invention can be enclosed in pressure resisting containers, which may be provided with metering valves. The propellant and the other ingredients of the composition can be selected with thought to the temperature at which the composition shall be used.

Before being used, the compositions of the present invention may also be maintained at a temperature lower than the boiling point of the propellant or the mixture of propellants, and when used be given a temperature which is at least equal to the boiling point of the propellant or the mixture of propellants.

What I claim is:

1. A composition for forming foam, consisting essentially of a mixture of:
   1. at least one member selected from the group consisting of p-xylene, 1-decanol, oleic acid, cholesterol, butanol and caprylic acid,
   2. water,
   3. a liquefied propellant selected from the group consisting of fluoro and chloro substituted alkanes having 1 - 4 carbon atoms, and
   4. at least one surface active agent selected from the group consisting of 1-amino octane, sodium oleate, decaethylene glycol, sodium caprylate and lecithin, in such proportions as to obtain a mesomorphic phase,
   said mesomorphic phase representing at least about 5 percent by weight of the mixture, and
   said propellant being dissolved in the mesomorphic phase in an amount of at least 2 percent by weight of the mixture.

2. A composition for forming foam, consisting essentially of a mixture of:
   1. at least one member selected from the group consisting of p-xylene, 1-decanol, oleic acid, cholesterol, butanol and caprylic acid;
   2. water,
   3. a liquefied propellant selected from the group consisting of propane, n-butane, iso-butane, n-pentane, iso-pentanes and n-hexane; and
   4. at least one surface active agent selected from the group consisting qf 1-amino octane, sodium oleate, decaethylene glycol, sodium caprylate and lecithin, in such proportions as to obtain a mesomorphic phase,
   said mesomorphic phase representing at least about 5 percent by weight of the mixture, and
   said propellant being dissolved in the mesomorphic phase in an amount of at least 2 percent by weight of the mixture.

3. A composition according to claim 1 wherein the percentages of the ingredients (1), (2), (3) and (4) are as follows:
   1. 1–55%
   2. 1.0–80%
   3. 2–15%
   4. 20–95%.

4. A composition according to claim 2 wherein the percentages of the ingredients (1), (2), (3) and (4) are as follows:
   1. 1–55%
   2. 1.0–80%
   3. 2–15%
   4. 20–95%.

5. A composition according to claim 1 wherein the amounts of components (1), (2) and (4) is as follows:
   30–60% water
   1–10% p-xylene
   40–70% 1-aminooctane.

6. A composition according to claim 1 wherein the amounts of components (1), (2) and (4) is as follows:
   20–80% water
   1–25% 1-decanol
   20–80% sodium oleate.

7. A composition according to claim 1 wherein the amounts of components (1), (2) and (4) is as follows:
   15–40% water
   15–30% oleic acid
   20–70% decaethylene glycol.

8. A composition according to claim 1 wherein the amounts of components (1), (2) and (4) is as follows:
   30–50% water
   10–30% butanol
   30–50% sodium caprylalte.

9. A composition according to claim 1 wherein the amounts of components (1), (2) and (4) is as follows:
   1–50% water
   1–22% cholesterol
   40–95% lecithin.

10. A composition according to claim 1 which in addition to the propellant consists of
    10–60% water
    1–55% caprylic acid
    30–75% 1aminooctane.

11. A composition according to claim 1 consisting essentially of a mixture of
    10–45% water
    5–50% caprylic acid
    40–85% 1-aminooctane
    2–15% dichlorotetrafluoroethane.

* * * * *